United States Patent [19]
LeHuec et al.

[11] Patent Number: 6,156,037
[45] Date of Patent: Dec. 5, 2000

[54] ANTERIOR LATERAL SPINE CAGE-PLATE FIXATION DEVICE AND TECHNIQUE

[75] Inventors: Jean-Charles LeHuec, Bordeaux; Mingyan Liu, Bourg-la-Reine; Loïc Josse, Palaja, all of France

[73] Assignee: SDGI Holdings, Inc., Memphis, Tenn.

[21] Appl. No.: 09/181,362

[22] Filed: Oct. 28, 1998

[51] Int. Cl.[7] .................................................. A61B 17/56
[52] U.S. Cl. ................................. 606/61; 606/69; 606/72
[58] Field of Search ................... 606/61, 69, 72, 606/73

[56] References Cited

U.S. PATENT DOCUMENTS

| | | | |
|---|---|---|---|
| D. 378,409 | 3/1997 | Michelson . | |
| 5,324,290 | 6/1994 | Zdeblick et al. | 606/61 |
| 5,569,247 | 10/1996 | Morrison | 606/61 |
| 5,676,666 | 10/1997 | Oxland et al. | 606/61 |
| 5,683,391 | 11/1997 | Boyd | 606/61 |
| 5,772,661 | 6/1998 | Michelson | 606/61 |
| 5,776,196 | 7/1998 | Matsuzaki et al. | 606/61 |
| 5,776,197 | 7/1998 | Rabbe et al. | 606/61 |
| 5,776,198 | 7/1998 | Rabbe et al. | 606/61 |
| 5,782,919 | 7/1998 | Zdeblick et al. | 623/17 |
| 5,904,683 | 5/1999 | Pohndorf et al. | 606/61 |

*Primary Examiner*—Gary Jackson
*Assistant Examiner*—Duphna Shai
*Attorney, Agent, or Firm*—Woodard, Emhardt, Naughton Moriarty & McNett

[57] ABSTRACT

An interbody fusion cage has an externally threaded stem projecting from a domed outer end. A contoured plate is provided with an aperture receivable on the stem. The stem threads receive a nut to fix the plate to the cage. Bone screws anchor the plate to vertebral bodies. A hemispherical surface on the plate and surrounding the stem-receiving aperture and bearing on the dome, accommodates universal angulation of the plate relative to the cage. In addition to a cage installation tool, there is a plate installation tool assembly including a cage installer, a plate holder, a nut holder and cage adjuster, a nut driver, and a plate holding prong controller.

36 Claims, 7 Drawing Sheets

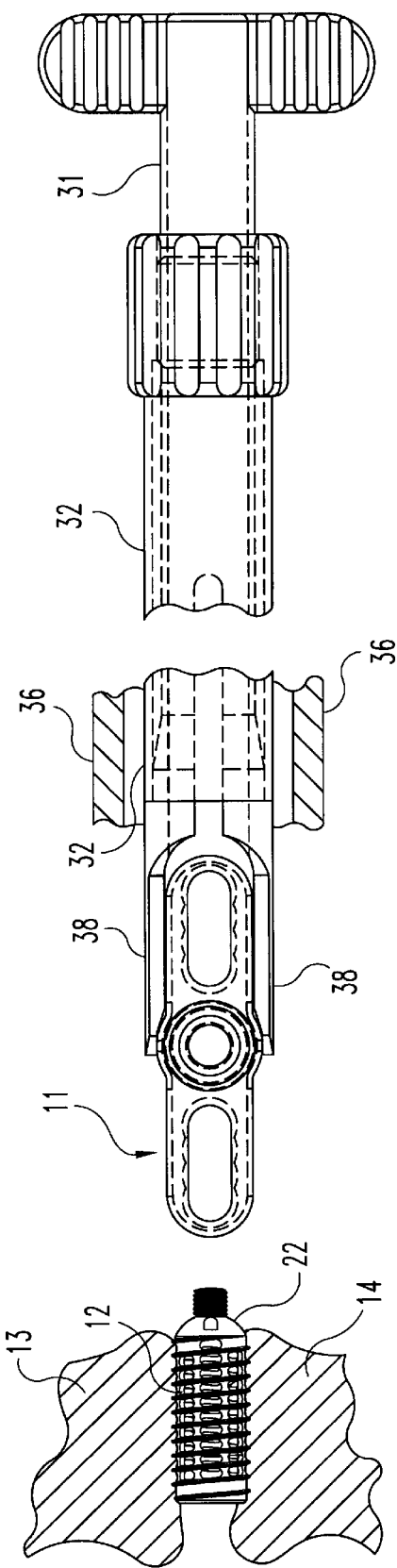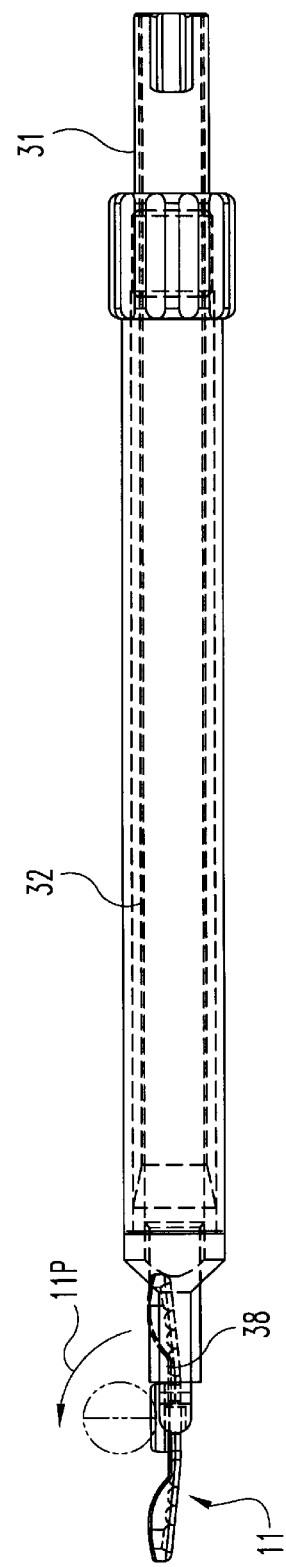

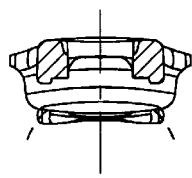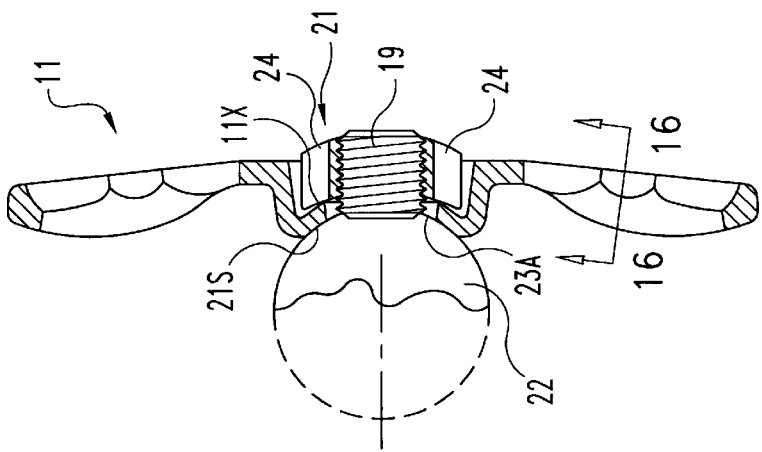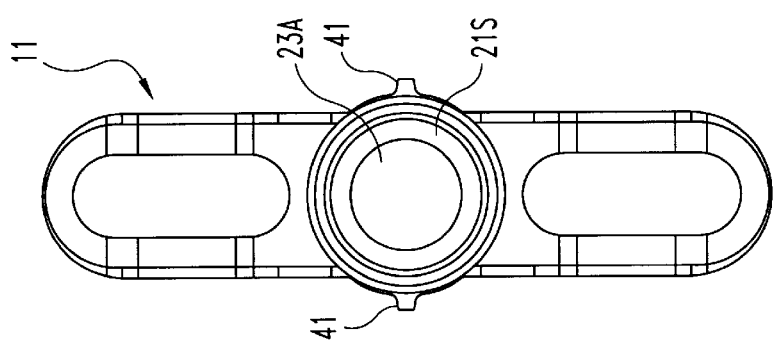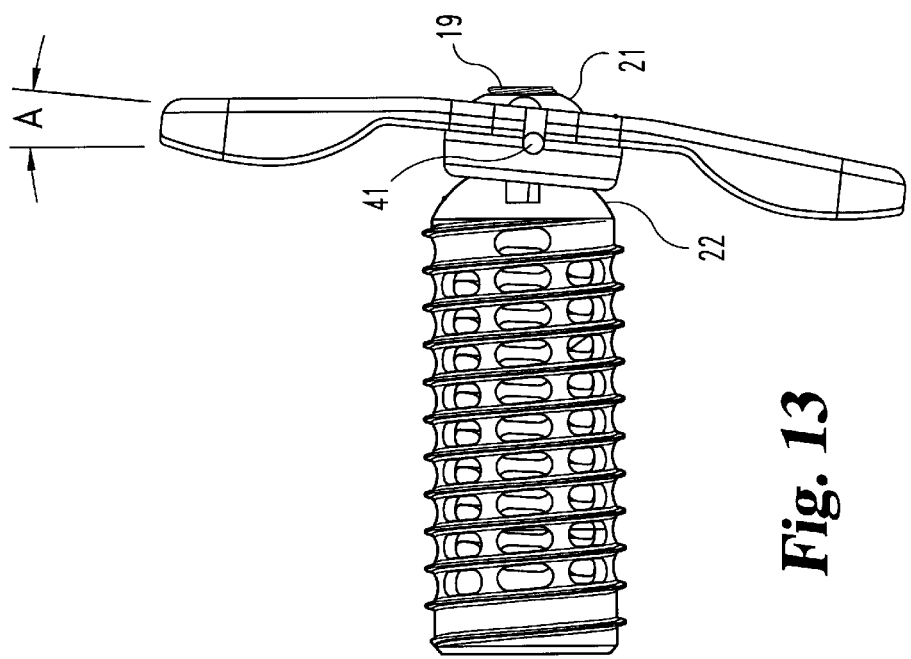

6,156,037

ANTERIOR LATERAL SPINE CAGE-PLATE FIXATION DEVICE AND TECHNIQUE

BACKGROUND OF THE INVENTION

In the art of spinal surgery, various devices and methods for interbody fusion have been developed and are described in literature. U.S. Pat. No. 5,772,661 issued Jun. 30, 1998 to Michelson is an example. U.S. Pat. No. 5,683,391 issued Nov. 4, 1997 to Lawrence M. Boyd describes a system for attachment of cylindrical interbody fusion devices to a spinal rod to which bone screws are also attached and anchored in the vertebral bodies. It is desirable that an interbody fusion construct be as stable as possible. Also, it is desirable to use an endoscopic procedure, if possible. It is an object of the present invention to provide a system for achieving these benefits.

SUMMARY OF THE INVENTION

According to one feature of the invention, an interbody fusion cage has an externally threaded stem projecting from a domed outer end. A contoured plate is provided with an aperture receivable on the stem. The stem threads receive a nut to fix the plate to the cage. The plate has additional apertures receiving bone screws anchoring the plate to vertebral bodies. The plate has a hemispherical surface surrounding the stem-receiving aperture and bearing on the dome, accommodating universal angulation of the plate relative to the cage.

According to another feature of the invention, and to implement the inventive method, a plate installation tool assembly including a plate holder, a nut holder and cage adjuster, a nut driver, and a plate holding prong controller, are arranged for simultaneous introduction through a single portal and operated during a minimally invasive endoscopic procedure for fitting the plate to vertebral bodies and connection of the plate to the cage.

BRIEF DESCRIPTION OF THE DRAWINGS

FIG. 11 is a schematic view of the plate holder with the plate oriented thereon longitudinally with the plate holder during introduction to the operation site.

FIG. 12 is an elevational view of the plate holder and plate rotated 90° about the longitudinal axis from the orientation shown in FIG. 11.

FIG. 13 is an elevational view of the plate-cage assembly illustrating the angulation feature of the invention.

FIG. 14 is a longitudinal section through the plate and nut and cage end connection taken at line 14—14 in FIG. 1 and viewed in the direction of the arrows.

FIG. 15 is a rear elevational view of the plate.

FIG. 16 is a cross sectional view of the plate at line 16—16 in FIG. 14 and viewed in the direction of the arrows.

DESCRIPTION OF THE PREFERRED EMBODIMENT

Figure 1:
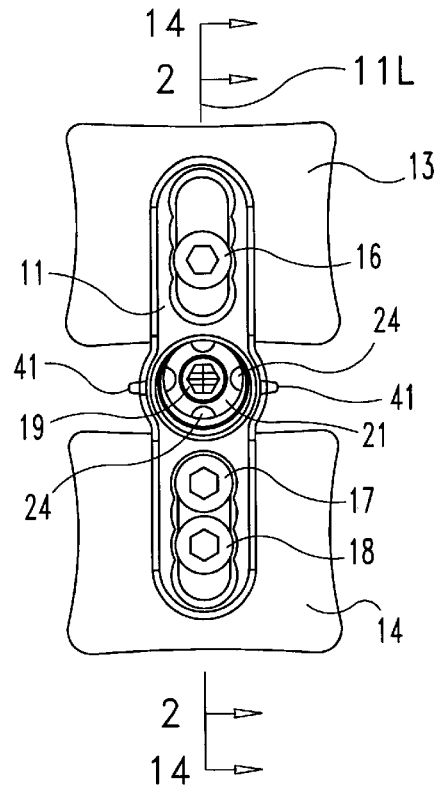
FIG. 1 is a schematic illustration of a spine cage-plate assembly in place with two vertebral bodies.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
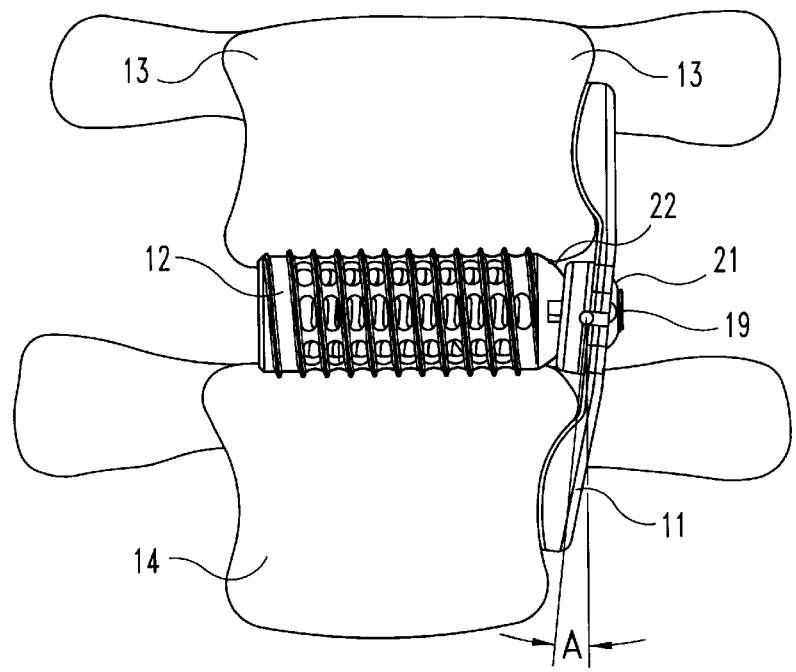
FIG. 2 is a section therethrough taken at line 2—2 in FIG. 1 and viewed in the direction of the arrows.
Figure 3:
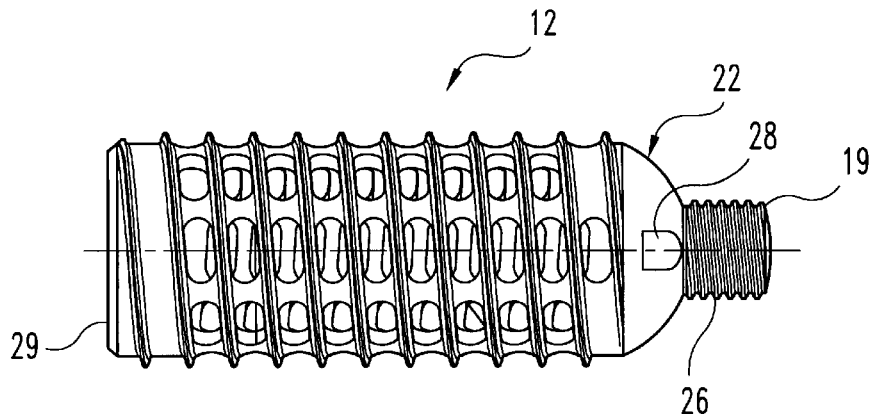
FIG. 3 is an elevational view of the cage itself.
Figure 4:
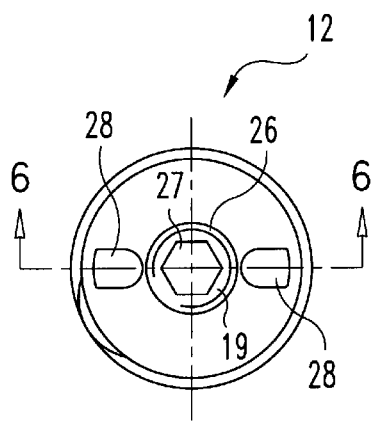
FIG. 4 is an outer end view thereof.
Figure 5:
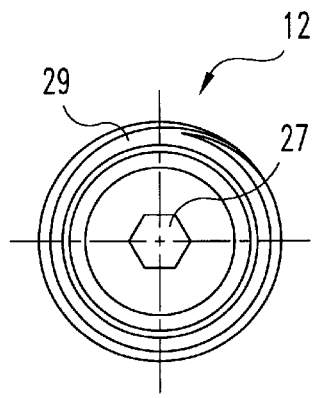
FIG. 5 is an inner end view thereof.
Figure 6:
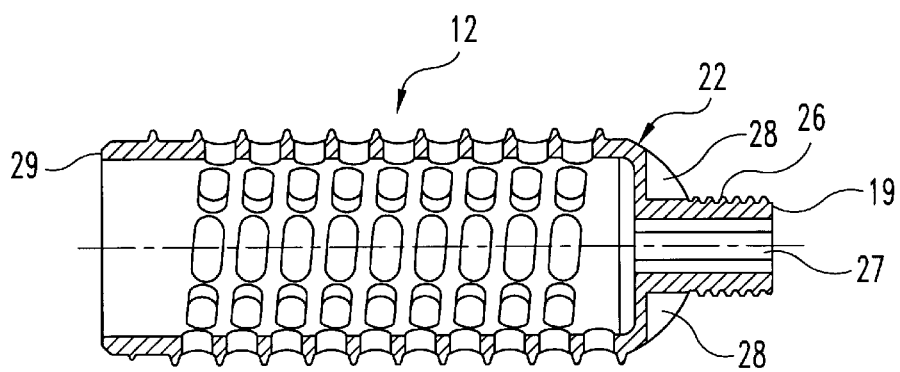
FIG. 6 is a longitudinal section therethrough taken at lines 6—6 in FIG. 4 and viewed in the direction of the arrows.

Referring now to the drawings in detail, FIGS. 1 and 2 show a finished installation of the plate 11 and cage 12 with two vertebral bodies 13 and 14. The plate is held to the vertebral bodies by bone screws 16, 17 and 18. The cage has a threaded stem 19 received through the center aperture 11A (FIG. 15) of the plate. The stem receives a nut 21 which secures the plate to the cage. The cage has a convex domed outer end 22 which receives the concave inner face seating face 23 of plate 11. The nut 21 has four tool receiver notches 24 circularly spaced on the outer face thereof for installation of the nut 21 on the threaded stem 19, as will be described.

Figure 9:
FIG. 9 is a view thereof similar to FIG. 7 but with the distal portion of a plate holder prong on the near side broken away to show the location of a plate lock nut on a nut driver prior to installation of the nut on a cage stem.
Figure 7:
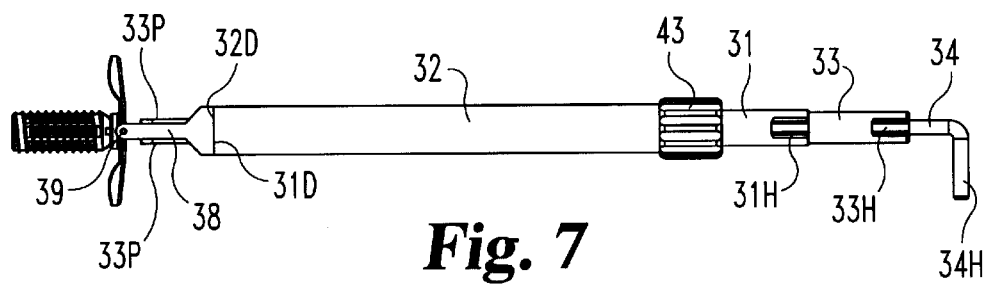
FIG. 7 is an elevational view of an installation tool assembly.

Referring now to FIGS. 3–6, various views of the cage are shown. In some respects, it is similar to and installed in much the same manner as cage I shown in FIGS. 18 and 19 of the above-mentioned U.S. Pat. No. 5,727,661 issued Jun. 30, 1998 to Michelson, the disclosure of which is incorporated herein by reference to any extent which may be needed to understand the device and method of the present invention. But in contrast to the implant I in the Michelson reference, the implant 12 of the present invention has a domed end 22 and a stem 19 externally threaded at 26 projecting therefrom. The domed end and stem have a tool receiver aperture 27 therein which, in the illustrated example, is hexagonal in shape. It also has two tool receiver notches 28 in the external domed face of the closed end of the implant. The opposite end 29, which is the internal end of the implant as installed, is open as shown. The external screw thread and cage wall apertures shown are such as now known in the art. Interbody implant types other than the cage type shown, might be used FIGS. 7 through 9, show a tool assembly for the installation and attachment of the plate to the cage. These include a plate holder 31, a constrictor tube 32, a nut driver tube 33 and an adjuster shaft 34. For endoscopic use of the present invention, all of these components may be introduced simultaneously through a surgical portal tube 36 (FIG. 11). The plate holder 31 is a tubular device with two diametrically opposed, longitudinally extending slots 31S (FIGS. 8 and 8A) therein. There are two prongs 38, each of which has a hole 39 therethrough. These receive pins 41 (FIGS. 1 and 15), one on each side of the plate 11 and integral with the plate, to permit pivoting of the plate from the inline position shown in FIGS. 11 and 12, to the transverse position shown in FIGS. 1, 2 and 7 through 9. The diameter of the plate holder steps down at shoulder 31D from a maximum diameter to a cylindrical surface 31C and then a conical surface 31L to the diameter extending out to the T-handle 31H. The plate holder, being slotted at 31S is made so that the prongs 38 are normally spread as at the dotted lines 38S (FIG. 8) for clearance of the pins 41 on the plate to enable insertion of the plate into the holder. Then the pins can be received in the holes 39 in the prongs when the distal end of the plate holder and prongs are constricted to the solid line illustration. This is done by moving the constrictor tube 32 in the direction of arrow 42, relative to the plate holder 31, whereupon the distal edge 32D of the constrictor tube operates on the conical surface 31L of the plate holder to drive the prongs 38 toward each other and thereby receive the pivot pins 41 of the plate in prong holes 39. Then the plate 11 can be pivoted to the inline introduction position on the plate holder wherein the longitudinal axis 11L (FIGS. 11 and 15) of the plate is colinear with the longitudinal axis of the plate holder 31. Knob 43 which is longitudinally confined on the constrictor tube 32, but rotatable thereon, is internally threaded for reception on an externally threaded portion 31E of the plate holder to facilitate the relative movement lengthwise between the constrictor tube 32 and the plate holder in the direction of the arrow 42, from an original position shown by the dotted outline 43S to the solid line position shown in FIGS. 7,8 and 9 to close the prongs onto the pivot pins 41 of the plate 11.

The nut driver 33 is slidably received inside the tube of the plate holder 31 and has two or four circularly spaced prongs 33P receivable in the axially extending tool receiver notches 24 of the nut 21 which is shown received in those prongs. These enable the use of the T-handle 33H on the nut driver to drive the nut onto the threaded post 19 of the cage.

The adjuster 34 has an L-shaped handle 34H at the proximal end. It has a distal end portion 34E (FIG. 8A) of hexagonal cross-section sized for reception in the tool receiver hole 27 of the cage. It has an external thread 34T on which the nut 21 is temporarily mounted as shown by the solid lines in FIGS. 7,8 and 9, and dotted in FIG. 8A. Thread 34T is of exactly the same diameter and pitch as the thread 26 on the cage stem 19. When the hexagonal tool end portion 34E is received in the mating hexagonal hole 27 of the cage, the thread 34T on the adjuster is precisely aligned with the thread on cage stem 19, so that the nut 21 can be advanced, when desired, from the thread on the adjuster 34 onto the stem 19 to fasten the plate to the cage.

An important feature of the invention is that the plate have omni-directional angulation with respect to the cage. For this purpose, the outer end of the cage is domed at 22 and the inner face of the plate is shaped to fit the dome but permit tilt from the cage axis to the extent needed to facilitate attachment to the vertebral bodies. The wings of the plate are contoured at 11C in a curve about axes perpendicular to a plane containing the longitudinal axis 11L of the plate and the axis of the center aperture 11A of the plate. The spherical radius of the internal seating face 23 of the plate may be slightly less than the spherical radius of the dome face 22 of the cage. The central stem-receiving aperture 11A of the plate may be sufficiently larger than the outer diameter of the stem threads 26 to accommodate the slight off-axis movement of the plate relative to the cage when a nonperpendicular attitude of the plate relative to the cage axis is needed such as shown, for example, in FIGS. 13 and 17. The arrangement may accommodate an angulation, as shown at A in FIG. 13, of as much as 10 degrees, for example.

Figure 8A:
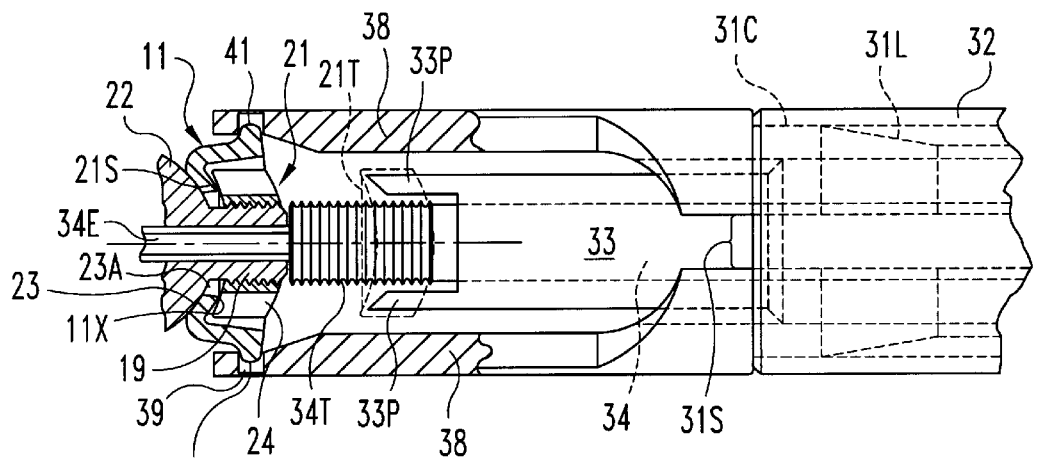
FIG. 8A is an enlarged fragmentary sectional view of a portion of FIG. 8 and showing the details of the connection between the cage and plate.
Figure 8:
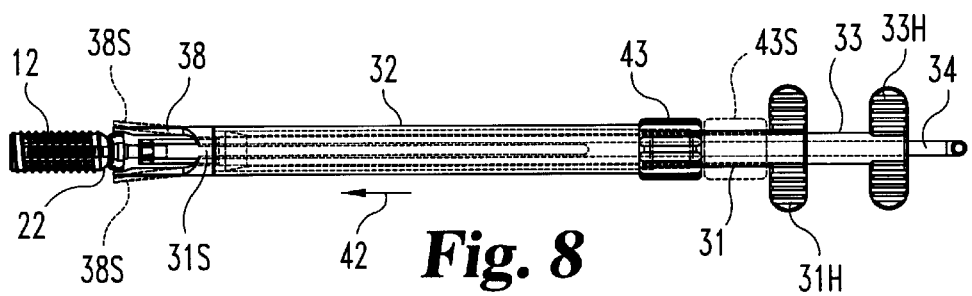
FIG. 8 is a view thereof rotated 90° on its longitudinal axis.

FIG. 13, which is a section through the plate and nut assembly similar to FIG. 8A but taken at line 13—13 in FIG. 1 and without the stem showing, shows that the nut 21 also has a concave seating face 21S which seats on the convex face 11X on the outside face of the wall whose inside seating face 23 engages the dome 22 of the cage. Thus, the nut can accommodate the tilting of the plate while the nut remains securely on the axis of the stud. The outer face 21F of the nut is convex to facilitate capture in the concave surface of the distal end wall of the nut driver 33S immediately adjacent each of the prongs 33P to better accommodate the prongs in the notches 24 of the nut when tightening it.

Procedure

Figure 10:
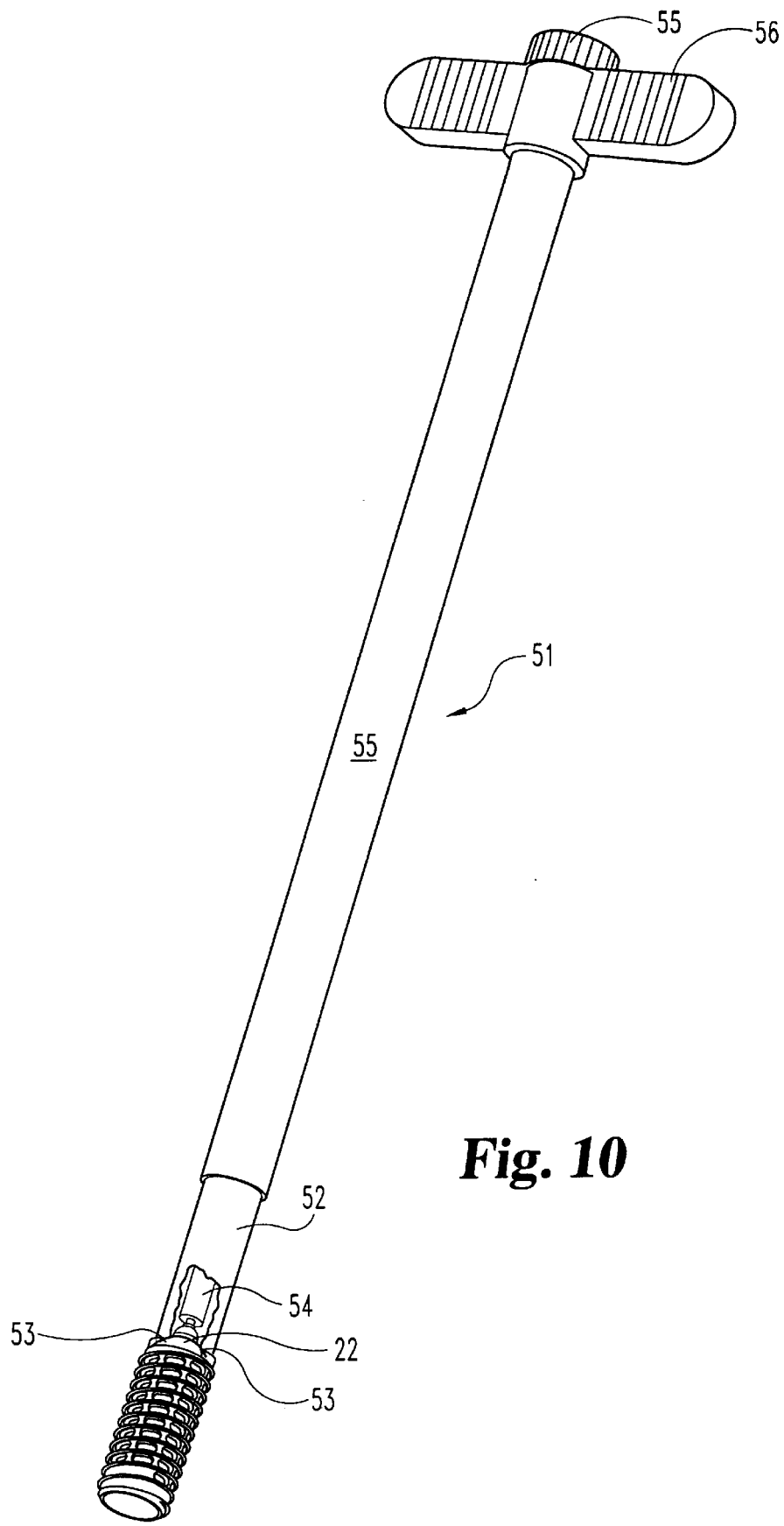
FIG. 10 is a perspective view of a cage installation tool.

Following the usual preparation of the patient for anterior lateral approach to the operation field, and where the procedure is to use an endoscopic approach, three or four small access openings are provided in the patient. A surgical portal 36 is located in one of the openings for introduction of the instruments for preparing the site for introduction of a cage, followed by introduction of the cage itself. The cage may be mounted to the tool 51 (FIG. 10) in which the domed end 22 of the cage is received in the distal end of portion 52 of the installation tool with the tabs 53 of the tool portion 52 received in the notches 28 of the cage, and an internally threaded distal end of the central shaft 54 in the tool threadedly engaged with the cage stem thread 26. The central shaft is rotatable by the knob 55 at the upper end of the shaft 54, whereby the cage can be pulled snug against the distal end of the tool portion 52. For installation in the intervertebral space, the cage is guided through the portal (36 in FIG. 11) and installed in the space in the usual manner, using the handle 56 to turn the cage into the space. Once the observer is satisfied that the cage has been installed properly, the knob 55 can be turned while the handle 56 is held stationary, to unscrew the shaft from the cage end stem. Then the installation tool 51 can be removed from the domed end of the cage and withdrawn from the portal.

With the cage in place, the tool assembly according to the present invention, is prepared for introduction through the portal. The adjuster shaft 34 is inserted through the proximal end of the nut driver 33. The nut 21 is screwed onto the thread 34T on shaft 34 at the proximal end of the hexagonal distal end portion 34E of the shaft 34. This assembly is inserted into the proximal end of the plate holder/constrictor tube assembly. The outer constrictor tube 32 is retracted on the plate holder tube 31 to a point near the handle 31H. As this is done, the prongs 38 expand to the dotted line position 38S and the plate 11 is installed between the prongs 38 and the pivot pins 41 on the plate are aligned with the apertures 39 in the prongs 38. Then the constrictor tube 32 is advanced in the direction of arrow 42 by turning the knob 43 on the tube, thus camming the prongs 38 to the closed position shown in FIGS. 7 through 9, 11 and 12.

After installation of the plate 11 on the plate holder 31, the plate is pivoted on prongs 38 to the inline position shown in FIGS. 11 and 12 where the longitudinal axis of the plate is colinear with the longitudinal axis of the plate holder. Then it is introduced through the portal 36 into the operation field. Then, by the use of forceps or other appropriate manipulators introduced through one of the other openings in the body, the plate is pivoted in the direction of arrow 11P in FIG. 12 to a position where its longitudinal axis is approximately perpendicular to the longitudinal axis of the cage.

Then the plate central aperture 11A is advanced onto the stem 19 of the cage by pushing the handle 31H in the direction of arrow 42.

Then, when the plate is situated with its convex surfaces 11C suitably positioned in the concave surfaces of the upper and lower vertebral bodies as viewed with the endoscope, the bone screws are installed by conventional procedures. Before tightening the bone screws, it is important to observe that the cage is installed in the intervertebral space deep enough that there is no stress upon contact of the seating surface 23 of the plate with the domed surface 22 of the cage. If the cage is not deep enough, then the handle 34H can be turned clockwise (for example), turning the hexagonal distal end 34E of shaft 34 which is received in the hexagonal receiver aperture 27 of the cage. So the cage can be turned enough to screw the cage deeper into the intervertebral space and avoid any stress that would be introduced upon tightening the bone screws to tighten the plate against each of the vertebral bodies.

Figure 17:
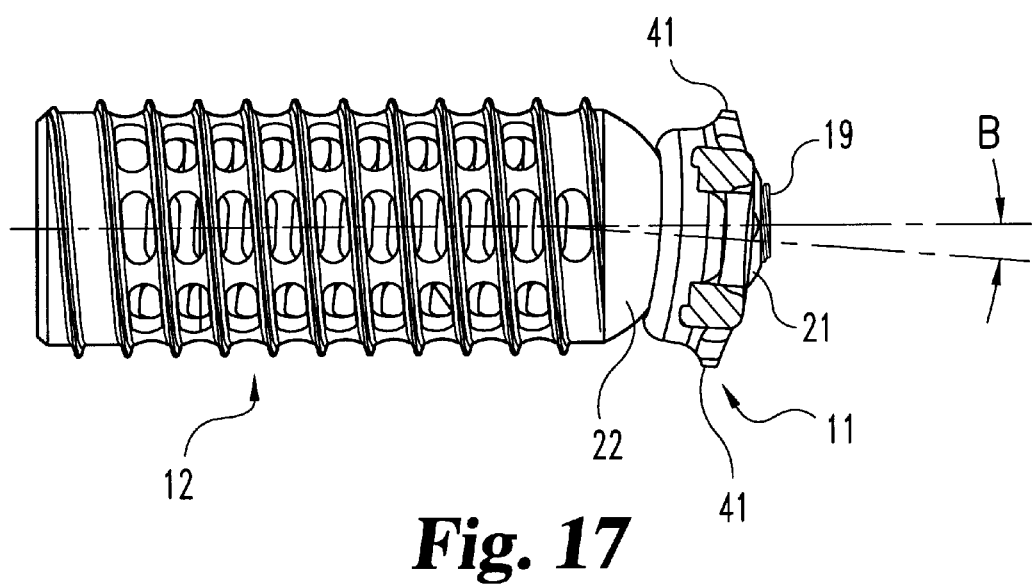
FIG. 17 is a cross-sectional view of the plate at line 16—16 in FIG. 14 and viewed in the direction of the arrows, just as in FIG. 16, but showing the cage too, and the attitude of the plate on the dome of the cage tilted in a plane perpendicular to the longitudinal axis of the plate.

Following the installation and tightening of the bone screws, the area of contact of the cage dome 22 with the plate seat 23 is inspected again to make sure that there is contact between the two parts so that there is no looseness at that location, yet no binding. If there remains a space between the two of them, then the handle 34H can be turned in the counterclockwise direction to pull the cage out slightly so that there is engagement between the two hemispherical surfaces of the dome and the plate for a secure fit. The domed nature of the cage and matching surface of the plate accommodate any needed angulation of the plate relative to the dome which might be needed to minimize or avoid stress on the intervertebral bodies, the plate or the cage. Then with the shaft handle 34H held to prevent turning of the cage, the nut driver handle 33H is turned in the clockwise direction with the end prongs 33P of the driver engaged in the grooves 24 in the nut, whereby the nut 21 is rotated clockwise to turn the nut off the thread 34T on shaft 34 and onto the thread 26 of the cage stem 19 which has been perfectly aligned with the shaft 34 due to the continued reception of the hexagonal distal end portion 34E of the shaft 34 in the receiver aperture 27 in the cage. Then the nut is tightened onto the plate by driver 33 while the cage is held stationary by the shaft 34. Because of the slight concave spherical surface on the inner face of the nut, it engages the spherical surface 11X of the plate and can readily accommodate the tilting of the plate, even though the nut remains aligned with the axis of the cage and the plate is tilted with respect to the axis of the cage such as shown in FIG. 13, for example. While mating convex and concave bearing surfaces of other shapes may be used, the angulation with the preferred spherical bearing surfaces 22 and 23 is universal, as demonstrated in FIG. 17 where the plate is tilted both upper and lower as shown in FIGS. 1 and 2 and 13 as well as in a posterior and anterior manner at angle B as shown in FIG. 17. In other words, upon installation and fitting to the vertebral bodies at the surgical site, the plate can be tilted relative to the cage, in a plane containing the axis of the cage, anywhere desired in the 360 degrees about the axis of the cage. After completion of the step of tightening the nut on the cage stem, the plate holder 31 is disconnected from the plate by retracting the constrictor tube 32 by turning the knob 43 thereon to permit the prongs 38 to spread to the dotted line position 38S to release them from the pivot pins 41 on the plate. Then the entire tool assembly of FIGS. 7, 8, and 9 can be removed from its position in the portal. Thus, the installation of the cage and plate have been completed.

The present invention provides a bone anchorage of an interbody fusion implant with a plating device. It allows bolt connection of a cage to a plate in any given angulation. It allows for open or endoscopic surgical approach. It provides easy and reliable connection between the implant and plate for increased stability of the interbody fusion construct. It permits minimally invasive lateral approach to the spine.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An interbody fusion assembly comprising:
   an interbody fusion device which is elongated, has a longitudinal axis, has an inner end and an outer end, and is adapted to be implanted in the intervertebral disc space between two vertebral bodies in a spine and to accommodate fusion of the disc space;
   a fastener receiver on the outer end;
   an attachment plate mounted on the outer end;
   said plate having first and second ends and first and second sites, respectively, thereon adjacent said ends, for attachment respectively to a first and second ones of said two vertebral bodies, and said plate and outer end of said fusion device having bearing surfaces shaped and inter-engaging such that said bearing surfaces facilitate various angulations of the plate relative to the longitudinal axis of the fusion device; and
   a fastener engaging the receiver and plate and connecting the plate to the device.

2. The assembly of claim 1 and wherein:
   the plate is elongate and has an aperture therein receiving the fastener receiver through the aperture.

3. The assembly of claim 2 and wherein:
   the fastener receiver is a threaded stem; and
   the fastener is a nut threaded onto the stem.

4. The assembly of claim 3 and wherein:
   the inter-engaging bearing surfaces are swivel bearing surfaces enabling various angulations of the plate relative to the fusion device and fixation at a selected angulation when the nut is tightened on the stem and against the plate.

5. The assembly of claim 4 and wherein:
   the inter-engaging swivel bearing surfaces of the plate and the outer end of the fusion device are shaped to provide universal angulation of the plate relative to the fusion device.

6. The assembly of claim 4 and wherein:
   the inter-engaging swivel bearing surface of the fusion device is a dome;
   the fusion device having a tool receiver on said dome to facilitate installation in the intervertebral disc space.

7. The assembly of claim 4 and wherein:
   the nut and plate have inter-engaging bearing surfaces accommodating tilting of the plate relative to the nut for fixation at said selected angulation.

8. The assembly of claim 7 and wherein:
   the nut has tool receiver notches in the outer face thereof for installation and tightening of the nut on the stem and against the plate.

9. The assembly of claim 8 and wherein:
   the outer face of the nut is convex for reception in a concave receiver surface of a nut driver.

10. The assembly of claim 7 and wherein:
said inter-engaging bearing surfaces of the nut and plate include a concave spherical surface on said nut.

11. The assembly of claim 10 and wherein:
said inter-engaging bearing surfaces of the nut and plate include a convex spherical surface on the plate.

12. The assembly of claim 11 and wherein:
the fusion device includes a generally cylindrical cage having an apertured wall and an external thread.

13. The assembly of claim 1 and wherein:
the device has a domed portion at the outer end serving as one of said bearing surfaces; and
the plate has the other of said bearing surfaces engaging the domed portion of the fusion device.

14. The assembly of claim 13 and wherein:
the domed portion of the device engaged by the bearing surface of the plate is spherical.

15. The assembly of claim 14 and wherein:
the bearing surface of the plate is spherical.

16. The assembly of claim 13 and wherein:
the plate is elongate, has a longitudinal axis, and has an aperture therein with an aperture axis perpendicular to the longitudinal axis, and has two wings extending out from the said aperture, the wings having inner bearing surfaces for engaging curved exterior surfaces of vertebral bodies, the inner bearing surfaces being contoured for mating with contours of vertebral bodies.

17. The assembly of claim 16 and wherein:
the contoured inner bearing surfaces are curved about axes perpendicular to a plane containing the longitudinal axis of the plate and containing the axis of the aperture.

18. The assembly of claim 16 and wherein:
the contoured inner bearing surfaces are curved about axes perpendicular to a plane containing the longitudinal axis of the plate and the longitudinal axis of the device.

19. In a subject having a spine including at least two vertebral bodies, a method of interconnection of bone anchorage, an interbody fusion device and a plate, the method comprising the steps of:
introducing into the intervertebral space between two vertebral bodies, a fusion device adapted to be implanted in the intervertebral disc space between the two vertebral bodies in the spine and to accommodate fusion in the disc space;
receiving through an aperture in the plate, a stem fixed to the fusion device;
mounting the plate on the fusion device and seating the plate with convex surfaces of the plate positioned in concave surfaces on the vertebral bodies;
applying plate anchors to the vertebral bodies and the plate;
tightening the anchors to the plate and the vertebral bodies;
applying a fastener to the stem and engaging the plate; and
tightening the fastener on the stem and plate and thereby fastening the plate to the fusion device.

20. The method of claim 19 and further comprising the steps of:
attaching the plate to the vertebral bodies with bone screws, and tightening the bone screws thereby anchoring the plate to the vertebral bodies.

21. The method of claim 20 and further comprising the step of:
adjusting the plate to the fusion device before tightening the bone screws.

22. The method of claim 19 and further comprising the steps of:
providing contact of a part-spherical seat on the fusion device with a part-spherical seat on the plate when the fastener is tightened on the stem and the plate.

23. The method of claim 19 and further comprising the steps of:
universally swiveling the plate on the fusion device before tightening the fastener on the stem and plate.

24. The method of claim 23 and wherein the swiveling step includes:
orienting the plate such that a longitudinal axis of the plate is at an angle between zero and ten degrees from a plane perpendicular to a longitudinal axis of the fusion device.

25. The method of claim 23 and further comprising the steps of:
providing contact of a part-spherical seat on the fusion device with a part-spherical seat on the plate when the fastener is tightened on the stem and the plate.

26. The method of claim 19 and further comprising the steps of:
before mounting the plate on the fusion device;
installing a nut driver onto an adjustment shaft;
threading a nut onto a distal end portion of the adjustment shaft;
installing the adjustment shaft with nut driver thereon into a plate holder and constrictor assembly;
spreading prongs at a distal end of the plate holder, and pivotally mounting the plate to the plate holder;
pivoting the plate on the plate holder to orient the plate inline with a longitudinal axis of the plate holder;
introducing the assembly of plate, plate holder, nut driver and adjusting shaft toward the fusion device;
pivoting the plate from the inline attitude to a transverse attitude relative to the plate holder as the plate is advanced to position against one of the vertebral bodies;
installing the device stem receiving aperture of the plate onto a stem of the fusion device;
fastening the plate to each of the vertebral bodies;
advancing the nut from the adjuster shaft onto the stem of the fusion device; and
tightening the nut on the stem and thereby securing the plate on the fusion device.

27. The method of claim 26 and further comprising the steps of:
prior to fastening the plate to the vertebral bodies,
using the adjuster shaft to move the fusion device in the intervertebral space and relative to the vertebral bodies in the direction of the axis of the fusion device to any extent necessary to establish sliding swivel contact between an outer end of the fusion device and an inner bearing face of the plate.

28. An interbody fusion assembly comprising:
an interbody fusion device having an inner end and an outer end and configured to be received in the intervertebral disc space between two vertebral bodies of a human spine;
an attachment device which has first and second ends and has first and second sites, respectively, thereon adjacent said ends, for attachment respectively to a first and second ones of the two vertebral bodies;

the attachement device and fusion device having inter-engaging bearing surfaces shaped for cooperating and accommodating various degrees of angulation between the attachment device and the fusion device, said bearing surface of the attachment device being located between the sites for attachment to vertebral bodies; and fasteners on said devices for fixing said attachment device and said fusion device together in a selected degree of angulation.

29. The assembly of claim 28 and wherein:

the bearing surfaces include a curved concave bearing surface on one of said device.

30. The assembly of claim 28 and wherein:

the fasteners for fixing said devices together include inter-engaging screw threads on said devices.

31. The assembly of claim 30 wherein:

said inter-engaging threads include a nut having an axis and curved bearing surface thereon engaging said attachment device around said axis while fixing said devices together, independent of the degree of angulation between the attachment device and the fusion device.

32. The assembly of claim 28 and wherein:

the fusion device has a domed portion at the outer end with an outwardly-facing bearing surface thereon; and the attachment device has an inwardly-facing bearing surface thereon engaging the bearing surface of the domed portion of the fusion device.

33. The assembly of claim 32 and wherein:

the fusion device has a threaded stem on one of said ends;

the attachment device is elongate and has an aperture therein receiving the stem through the aperture; and a nut threaded on the stem engages the attachment device and connects the attachment device to the fusion device, the aperture being large enough to enable movement of the attachment device on the domed portion to various positions wherein the stem is at various distances from edges of said aperture.

34. The assembly of claim 33 and wherein:

said attachment device has an outwardly facing domed bearing surface engaged by an inwardly facing concave bearing surface on said nut.

35. The assembly of claim 34 and wherein:

the fusion device is an apertured bone cage, and has a tool receiver in the stem to enable preventing rotation of the cage when the nut is rotated on the stem.

36. The assembly of claim 35 and wherein:

the attachment device is a plate having pivot surface thereon with a pivot axis transverse to the elongate dimension of the plate for reception and pivoting on a plate holder installation tool assembly.

* * * * *

UNITED STATES PATENT AND TRADEMARK OFFICE
CERTIFICATE OF CORRECTION

PATENT NO.     : 6,156,037
DATED          : December 5, 2000
INVENTOR(S)    : LeHue et al.

It is certified that error appears in the above-identified patent and that said Letters Patent is hereby corrected as shown below:

<u>Title page,</u>
Before "Primary Examiner", please insert:

-- FOREIGN PATENT DOCUMENTS
19630256     01/1998     Germany
2727005      05/1996     France
29511146     11/1995     Germany
2747035      10/1997     France
95/26164     05/1995     WIPO  --

<u>Column 9,</u>
Line 3, please change "attachement" to -- attachment --.
Line 15, please change "device" to -- devices --.

Signed and Sealed this

Second Day of July, 2002

Attest:

JAMES E. ROGAN
Attesting Officer     *Director of the United States Patent and Trademark Office*